(12) United States Patent
Holladay

(10) Patent No.: US 11,464,653 B2
(45) Date of Patent: Oct. 11, 2022

(54) MINIMALLY INVASIVE SURGERY (MIS) METHODS AND DEVICES

(71) Applicant: Innovasis, Inc., Salt Lake City, UT (US)

(72) Inventor: Frank Holladay, Kansas City, KS (US)

(73) Assignee: Innovasis, Inc., Salt Lake City, UT (US)

(*) Notice: Subject to any disclaimer, the term of this patent is extended or adjusted under 35 U.S.C. 154(b) by 150 days.

(21) Appl. No.: 16/916,927

(22) Filed: Jun. 30, 2020

(65) Prior Publication Data
US 2020/0405503 A1 Dec. 31, 2020

Related U.S. Application Data

(60) Provisional application No. 62/868,961, filed on Jun. 30, 2019.

(51) Int. Cl.
| | | |
|---|---|---|
| *A61F 2/46* | (2006.01) | |
| *A61F 2/44* | (2006.01) | |
| *A61F 2/30* | (2006.01) | |
| *A61B 17/16* | (2006.01) | |
| *A61B 17/34* | (2006.01) | |

(52) U.S. Cl.
CPC .......... *A61F 2/4611* (2013.01); *A61F 2/4455* (2013.01); *A61B 17/1671* (2013.01); *A61B 17/3423* (2013.01); *A61F 2002/30622* (2013.01); *A61F 2002/4635* (2013.01)

(58) Field of Classification Search
CPC .......... A61F 2/44; A61F 2/4455; A61F 2/446; A61F 2/4465; A61F 2/447; A61F 2/46; A61F 2/4603; A61F 2/4611; A61B 17/1659; A61B 17/1671
See application file for complete search history.

(56) References Cited

U.S. PATENT DOCUMENTS

| | | | |
|---|---|---|---|
| 9,642,720 B2 * | 5/2017 | Radcliffe | A61F 2/447 |
| 10,245,159 B1 * | 4/2019 | Kleiner | A61F 2/447 |
| 10,588,754 B2 * | 3/2020 | O'Neil | A61F 2/30771 |
| 10,925,592 B2 * | 2/2021 | Sandhu | A61B 17/3468 |
| 10,973,656 B2 * | 4/2021 | Kleiner | A61F 2/4455 |
| 2013/0144320 A1 * | 6/2013 | To | A61B 17/32002 606/190 |

(Continued)

*Primary Examiner* — Eric S Gibson
(74) *Attorney, Agent, or Firm* — Brooks, Cameron & Huebsch, PLLC

(57) ABSTRACT

Embodiments of the present disclosure includes method and devices for minimally invasive spinal fusion surgery. A method for minimally invasive spinal fusion surgery can include accessing a spinal column through a working channel device, wherein the working channel has a proximal end and a distal end, advancing the working channel so that the distal end pierces an outer layer of a vertebral disc, inserting a disc extractor through the working channel device and into the vertebral disc to cut the vertebral disc into pieces, inserting a disc blade through the working channel device and into the vertebral disc to cut the vertebral disc into pieces, using a disc rake to remove the pieces of the vertebral disc, inserting a disc shaver to clean a number of surfaces of vertebra adjacent to the vertebral disc, and inserting and implanting a disc implant in a space from where the vertebral disc was removed.

18 Claims, 5 Drawing Sheets

(56) References Cited

U.S. PATENT DOCUMENTS

| | | | |
|---|---|---|---|
| 2014/0052253 A1* | 2/2014 | Perloff | A61F 2/442 623/17.15 |
| 2014/0058512 A1* | 2/2014 | Petersheim | A61F 2/4611 623/17.16 |
| 2014/0257296 A1* | 9/2014 | Morgenstern Lopez | A61B 17/1757 606/80 |
| 2014/0277204 A1* | 9/2014 | Sandhu | A61F 2/447 606/86 A |
| 2014/0378980 A1* | 12/2014 | Lomeli | A61B 17/8811 606/90 |
| 2015/0045892 A1* | 2/2015 | Lynn | A61B 17/1671 623/17.16 |
| 2015/0100124 A1* | 4/2015 | Whipple | A61F 2/447 623/17.15 |
| 2015/0148907 A1* | 5/2015 | Kleiner | A61F 2/4455 606/94 |
| 2015/0173917 A1* | 6/2015 | Radcliffe | A61F 2/447 623/17.16 |
| 2016/0095721 A1* | 4/2016 | Schell | A61F 2/4684 623/17.16 |
| 2017/0065269 A1* | 3/2017 | Thommen | A61B 1/07 |
| 2017/0238984 A1* | 8/2017 | Kleiner | A61B 17/8805 |
| 2017/0360570 A1* | 12/2017 | Berndt | A61B 17/8858 |
| 2018/0028200 A1* | 2/2018 | O'Neil | A61F 2/446 |
| 2018/0042735 A1* | 2/2018 | Schell | A61F 2/4611 |
| 2018/0104072 A1* | 4/2018 | Squires | A61F 2/4465 |
| 2018/0333272 A1* | 11/2018 | Mirda | A61F 2/30771 |
| 2019/0021874 A1* | 1/2019 | Pimenta | A61F 2/4684 |
| 2019/0209154 A1* | 7/2019 | Richter | A61B 1/00091 |
| 2019/0224024 A1* | 7/2019 | Kleiner | A61F 2/4611 |
| 2019/0254836 A1* | 8/2019 | Cowan | A61F 2/4455 |
| 2019/0321055 A1* | 10/2019 | Seex | A61B 17/1671 |
| 2020/0008944 A1* | 1/2020 | Morgenstern Lopez | A61F 2/446 |
| 2020/0323559 A1* | 10/2020 | Skinner | A61B 17/3417 |
| 2020/0405501 A1* | 12/2020 | Orozco Castillo | A61B 17/686 |
| 2020/0405503 A1* | 12/2020 | Holladay | A61F 2/4455 |
| 2021/0068975 A1* | 3/2021 | Choi | A61B 17/025 |
| 2021/0077275 A1* | 3/2021 | Milella, Jr | A61F 2/4465 |
| 2021/0220149 A1* | 7/2021 | Kleiner | A61F 2/4601 |
| 2021/0307928 A1* | 10/2021 | Cohn | A61F 2/442 |
| 2021/0378837 A1* | 12/2021 | Morgenstern Lopez | A61L 27/3847 |

* cited by examiner

MINIMALLY INVASIVE SURGERY (MIS) METHODS AND DEVICES

PRIORITY INFORMATION

This application claims priority of U.S. Provisional Application Ser. No. 62/868,961, filed on Jun. 30, 2019, the contents of which are incorporated herein by reference.

TECHNICAL FIELD

The present disclosure relates to tools and methods for minimally invasive orthopedic spinal surgery.

BACKGROUND

Degenerative disc disease of the spine is common in the aging population and is a frequent cause of disability. Lumbar spondylosis, a defect or stress fracture in the pars interarticularis of the vertebral arch, can cause back pain and a poor quality of life. Surgical interbody fusion of degenerative levels is a treatment option to stabilize the painful motion segment and may provide indirect decompression of the neural elements. The surgical options for interbody fusion of the lumbar spine include: posterior lumbar interbody fusion (PLIF), transforaminal lumbar interbody fusion (TLIF), minimally invasive transforaminal lumbar interbody fusion (MI-TLIF), oblique lateral interbody fusion/anterior to psoas (OLIF/ATP), lateral lumbar interbody fusion (LLIF) and anterior lumbar interbody fusion (ALIF). In general, traditional posterior approaches are frequently used with acceptable fusion rates and low complication rates, however they are limited by thecal sac and nerve root retraction, along with iatrogenic injury to the paraspinal musculature and disruption of the posterior tension band. Minimally invasive (MIS) posterior approaches have evolved in an attempt to reduce approach related complications. Anterior approaches avoid the spinal canal, cauda equina and nerve roots, however, have issues with approach related abdominal and vascular complications. In addition, lateral and OLIF techniques have potential risks to the lumbar plexus and psoas muscle.

As discussed above, OLIF, or oblique lateral interbody fusion, is a less invasive approach to spinal fusion surgery in which the neurosurgeon accesses and repairs the lower (lumbar) spine from the front and side of the body (passing in a trajectory about halfway between the middle of the stomach and the side of the body). While patients have been provided with relief with this procedure, potential risks still exist.

DETAILED DESCRIPTION

Figure 1:
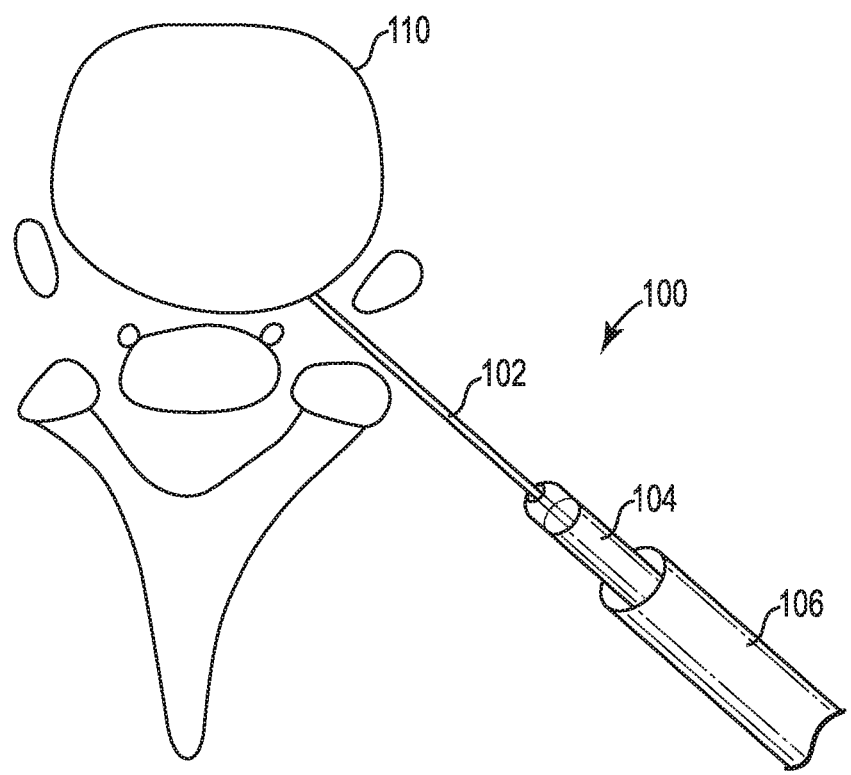
FIG. 1 illustrates a guide, a dilator, and a working channel device for minimally invasive spinal fusion surgery in accordance with embodiments of the present disclosure.

Embodiments of the present disclosure includes method and devices for minimally invasive spinal fusion surgery. A method for minimally invasive spinal fusion surgery can include accessing a spinal column through a working channel device, wherein the working channel has a proximal end and a distal end, advancing the working channel so that the distal end pierces an outer layer of a vertebral disc, inserting a disc extractor through the working channel device and into the vertebral disc to cut the vertebral disc into pieces, inserting a disc blade through the working channel device and into the vertebral disc to cut the vertebral disc into pieces, using a disc rake to remove the pieces of the vertebral disc, inserting a disc shaver to clean a number of surfaces of vertebra adjacent to the vertebral disc, and inserting and implanting a disc implant in a space from where the vertebral disc was removed.

A need exists for improvements in fusion procedures such as OLIF. Described herein are improved tools to allow the physician to better access, remove, and replace the disc. A disc extractor comprising a guide and a slide is disclosed. Tools including a disc rake, disc blade, and disc shaver are disclosed. After the disc has been removed, an implant is placed in the disc space.

Before describing various embodiments of the present disclosure in detail, it is to be understood that this disclosure is not limited to the parameters of the particularly exemplified implants, methods, systems and/or products, which may, of course, vary. Thus, while certain embodiments of the present disclosure will be described in detail, with reference to specific configurations, parameters, features (e.g., components, members, elements, parts, and/or portions), etc., the descriptions are illustrative and are not to be construed as limiting the scope of the claimed invention. In addition, the terminology used herein is for the purpose of describing the embodiments and is not necessarily intended to limit the scope of the claimed invention.

Unless defined otherwise, all technical and scientific terms used herein have the same meaning as commonly understood by one of ordinary skill in the art to which the present disclosure pertains.

Various aspects of the present disclosure, including implants, systems, processes, and/or products may be illustrated with reference to one or more embodiments or implementations, which are exemplary in nature. As used herein, the terms "embodiment" and "implementation" mean "serving as an example, instance, or illustration," and should not necessarily be construed as preferred or advantageous over other aspects disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

As used throughout this application the words "can" and "may" are used in a permissive sense (i.e., meaning having the potential to), rather than the mandatory sense (i.e., meaning must). Additionally, the terms "including," "having," "involving," "containing," "characterized by," as well as variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

It will be noted that, as used in this specification and the appended claims, the singular forms "a," "an" and "the" include plural referents unless the context clearly dictates otherwise. Thus, for example, reference to a "locking screw" includes one, two, or more locking screws.

As used herein, directional terms, such as "top," "bottom," "left," "right," "up," "down," "upper," "lower," "proximal," "distal," "vertical," "horizontal" and the like are used herein solely to indicate relative directions and are not otherwise intended to limit the scope of the disclosure and/or claimed invention Various aspects of the present disclosure can be illustrated by describing components that are bound, coupled, attached, connected, and/or joined together. As used herein, the terms "bound," "coupled", "attached", "connected," and/or "joined" are used to indicate either a direct association between two components or, where appropriate, an indirect association with one another through intervening or intermediate components. In contrast, when a component is referred to as being "directly bound," "directly coupled", "directly attached", "directly connected," and/or "directly joined" to another component, no intervening elements are present or contemplated. Furthermore, binding, coupling, attaching, connecting, and/or joining can comprise mechanical and/or chemical association.

To facilitate understanding, like reference numerals (i.e., like numbering of components and/or elements) have been used, where possible, to designate like elements common to the figures. Specifically, in the exemplary embodiments illustrated in the figures, like structures, or structures with like functions, will be provided with similar reference designations, where possible.

The figures herein follow a numbering convention in which the first digit or digits correspond to the figure number and the remaining digits identify an element or component in the figure. Similar elements or components between different figures can be identified by the use of similar digits. For example, 106 can reference element "06" in FIG. 1, and a similar element can be referenced as 306 in FIG. 3. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

Specific language will be used herein to describe the exemplary embodiments. Nevertheless, it will be understood that no limitation of the scope of the disclosure is thereby intended. Rather, it is to be understood that the language used to describe the exemplary embodiments is illustrative only and is not to be construed as limiting the scope of the disclosure (unless such language is expressly described herein as essential). Furthermore, multiple instances of an element and or sub-elements of a parent element may each include separate letters appended to the element number. An element label with an appended letter can be used to designate an alternative design, structure, function, implementation, and/or embodiment of an element or feature without an appended letter. Likewise, an element label with an appended letter can be used to indicate a sub-element of a parent element. However, element labels including an appended letter are not meant to be limited to the specific and/or particular embodiment(s) in which they are illustrated. In other words, reference to a specific feature in relation to one embodiment should not be construed as being limited to applications only within said embodiment.

Furthermore, multiple instances of the same element may each include separate letters appended to the element number. For example, two instances of a particular element "20" may be labeled as "20a" and "20b". In that case, the element label may be used without an appended letter (e.g., "20") to generally refer to every instance of the element; while the element label will include an appended letter (e.g., "20a") to refer to a specific instance of the element.

It will also be appreciated that where multiple possibilities of values or a range a values (e.g., less than, greater than, at least, or up to a certain value, or between two recited values) is disclosed or recited, any specific value or range of values falling within the disclosed range of values is likewise disclosed and contemplated herein.

Spinal fusion is performed to join together two or more bones of the spine, called vertebrae, eliminating movement between them. This is done by removing the intervertebral disc between the two vertebrae, which normally enables the spine to bend and rotate, and inserting a bone graft in its place. The bone graft heals over several months, fusing the vertebrae together and stabilizing the spine.

During an oblique lateral interbody fusion, or OLIF, procedure, the surgeon uses a corridor between the psoas muscle and the peritoneum to access the spine. The psoas muscles connect the lower back to the thighs and enable movement and flexibility of the back, pelvis, legs, and hips. The peritoneum is the membrane that lines the abdominal cavity. Once the disc is accessed, the surgeon uses various tools to remove the disc and to prepare site for the implantation of an implant that will be left in place to fuse the adjacent vertebrae together.

Usually, OLIF is recommended for the L2-L5 levels for most patients and for the L5-S1 levels for certain patients. Typically, the patient is placed on their side, with the left side up, for OLIF surgery. The surgery is generally used with fluoroscopy or image guided navigation.

To access the disc, a small incision is made, and the surgeon spreads the various muscle fibers until the psoas muscle is reached. A K-wire or other guide or access wire is used to access the target disc. In some embodiments, the guide can be an insulated device that allows for controlled electrical energy at the tip. This can be used to ensure that the psoas muscle and the nerve that are near it are avoided. The guide is placed into the disc to secure its location.

FIG. 1 illustrates a guide, a dilator, and a working channel device for minimally invasive spinal fusion surgery in accordance with embodiments of the present disclosure. The surgery can be as a minimally invasive oblique lateral interbody fusion (OLIF) surgery, for example. As shown in FIG. 1, spinal fusion surgery device 100 can include guide 102, which can be a K-wire, is used to access the vertebral disc 110 and is placed in vertebral disc 110. Next, a dilator 104 is placed over the guide 102. Dilator 104 is used to spread the muscles and other body tissues to accommodate the working channel device 106, which advanced over the dilator 102. In some embodiments, retractor blades (not shown) are used to provide an access channel. Working channel device 106 can include a proximal end and a distal end and the distal end of working channel device 106 can pierce an outer layer of a vertebral disc. Once the disc has been accessed and the working channel device 106 is in place, the wire 102 and dilator 104 can be removed.

Figure 2A:
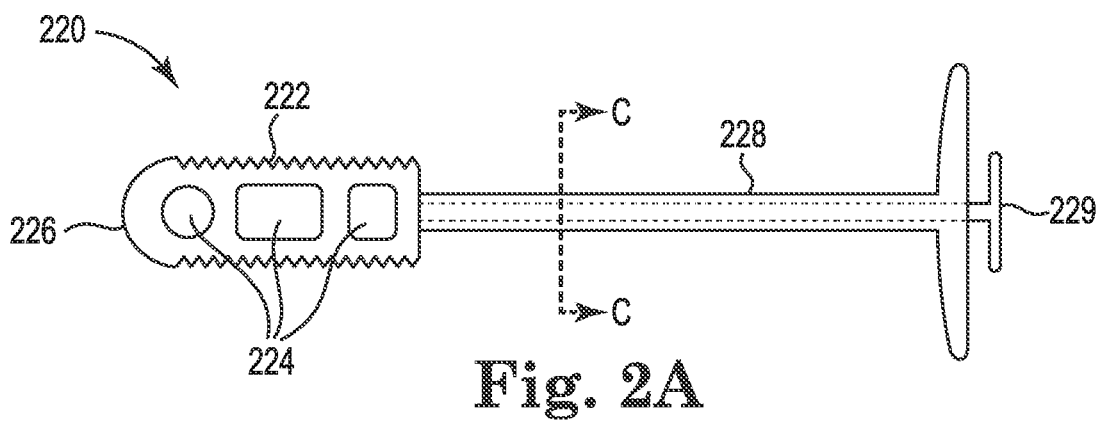
FIGS. 2A-2D illustrate a disc extractor for minimally invasive spinal fusion surgery in accordance with embodiments of the present disclosure.
Figure 2B:
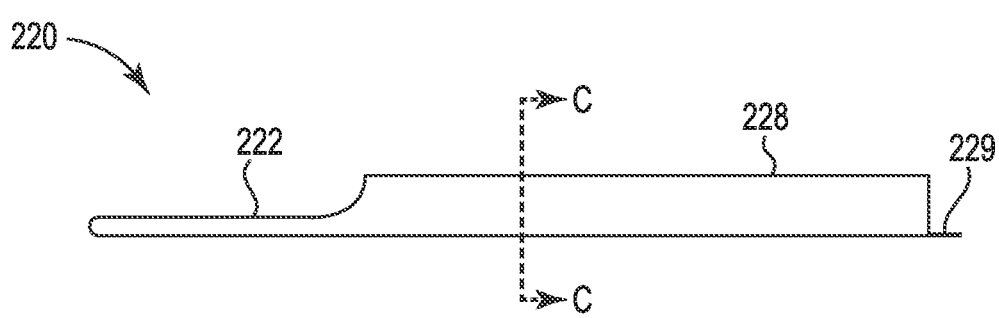
Figure 2C:
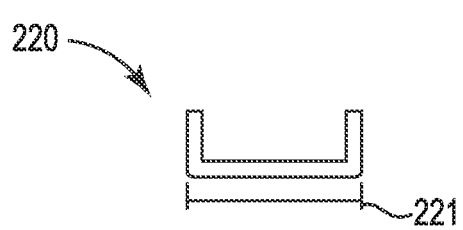
Figure 2D:
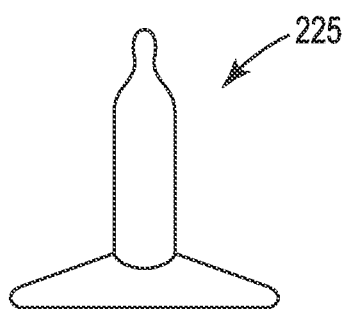

FIGS. 2A-2D illustrate a disc extractor for minimally invasive spinal fusion surgery in accordance with embodiments of the present disclosure. FIG. 2A is a top view of disc extractor 220. FIG. 2B is a side view of disc extractor 220. FIG. 2C is a cross-section view of shaft 228 of disc extractor 220. Disc extractor 220 comprises a serrated distal end 226, a shaft 228, and a handle assembly 229. FIG. 2D is a dilator 225 that can be positioned on the distal end 222 of disc extractor 220 to assist in making an opening in the exterior of disc (e.g., disc in FIG. 1 110), if necessary. Disc extractor 220 can have a width 221 of about 9 mm, but can be from 5 to 13 mm wide, depending on the application. As seen in the side view of FIG. 2B, the distal end 22 is relatively flat. The U-shaped channel of the shaft 228 is shown in the cross-section view of FIG. 2C. In a number of embodiments, extractor tip 226 has serrated edges 222 and openings 224, which aid in cutting the disc into pieces. Using the handle 229, the surgeon can advance and/or retract disc extractor 220 to gently cut the disc. Disc extractor 220 can also be rotated using handle 229 to aid in cutting the disc.

Figure 3:
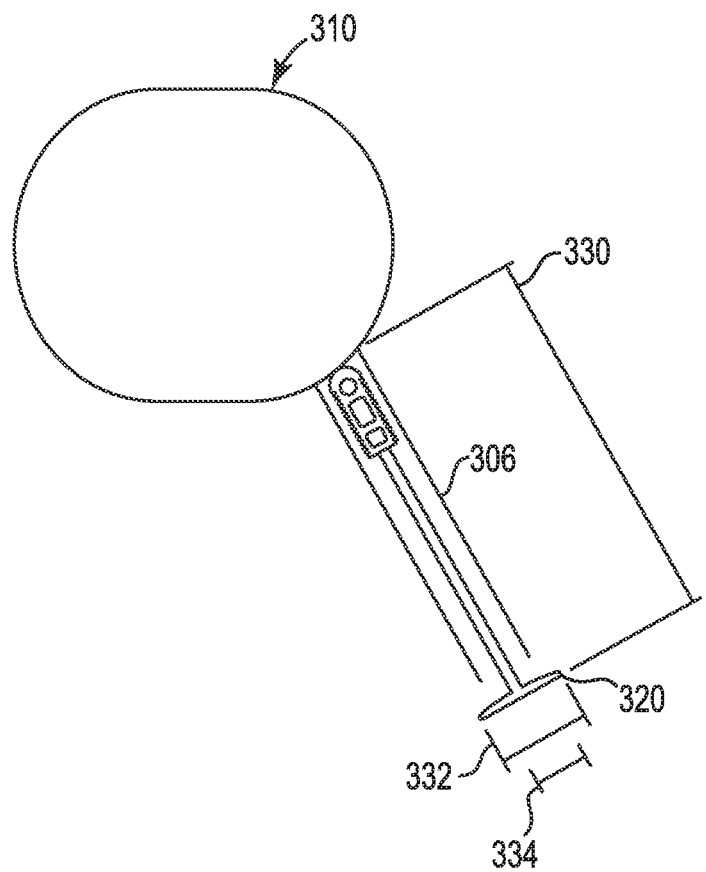
FIG. 3 illustrates a disc extractor accessing a disc via a working channel device in a minimally invasive spinal fusion surgery in accordance with embodiments of the present disclosure.

FIG. 3 illustrates a disc extractor accessing a disc via a working channel device in a minimally invasive spinal fusion surgery in accordance with embodiments of the present disclosure. In FIG. 3, disc extractor 320 is inside working channel device 306. The distal end of disc extractor 320 is engaged with disc 310 at the distal end of working channel 306. The handle on the proximal end of disc extractor 320 is protruding outside of the proximal end of working channel device 306 allowing the surgeon to hold and manipulate the disc extractor 320 via the handle of the disc extractor 320. As shown in FIG. 3, disc extractor 320 is advanced to the disc 310 via working channel device 306. Working channel device 306 can have a length 330 of about 23 cm, but can be from 16 to 30 cm, preferable from 21 to 25 cm, depending on the application. Working channel device 306 can have an inner diameter 334 of about 15 mm, but can be from 12 to 20 mm, and an outer diameter 332 of about 17 mm, but can be from 14 to 22 mm, depending on the application. Working channel device 306 can be configured to accommodate the tools of the present disclosure (e.g., the disc extractor, disc blade, disc rake, disc shaver, and/or delivery device) such that the tools can access the disc and the vertebra adjacent to the disc of a spinal column.

Figure 4A:
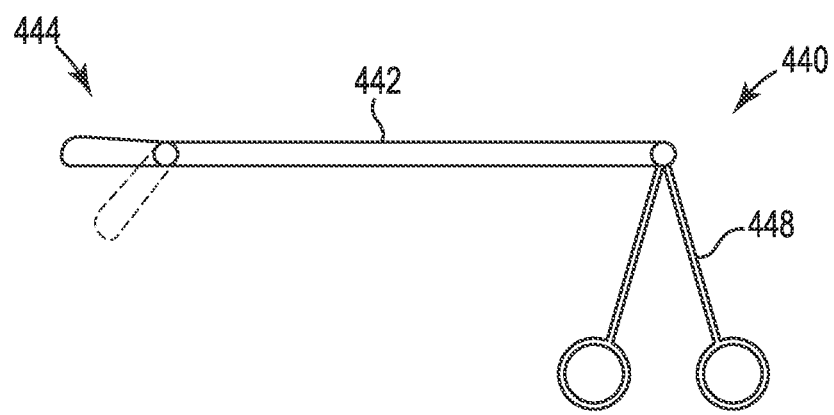
FIG. 4A illustrates a disc rake for minimally invasive spinal fusion surgery in accordance with embodiments of the present disclosure.

FIG. 4A illustrates a disc rake for minimally invasive spinal fusion surgery in accordance with embodiments of the present disclosure. To remove the pieces of the disc, disc rake 440 (e.g., a pituitary grasper) may be used. Shown in FIG. 4A is a disc rake 440 that can be used to remove the disc (e.g., pieces of the disc that was cut by the disc extractor and disc blade). In FIG. 4A, disc rake 440 comprises a distal tip 444, and elongate shaft 442, and a handle assembly 448. When manipulated, handle 448 opens and closes distal tip 444. As shown by the dotted lines in FIG. 4A, distal tip 444 can be arranged at an angle to shaft 442. Preferably the angle is about 45 to 75 degrees from the longitudinal axis of the shaft 442. Shaft 442 can be about 25 to 35 cm in length, more preferably about 28 to 32 cm in length. Distal end 444 can have two portions that can be opened and closed by actuation of handle 448 of the disc rake 440 to grasp and remove the pieces of the vertebral disc. The distal end 444 and shaft 442 of disc rake 440 can be configured to access the spinal column via a working channel device.

Figure 5A:
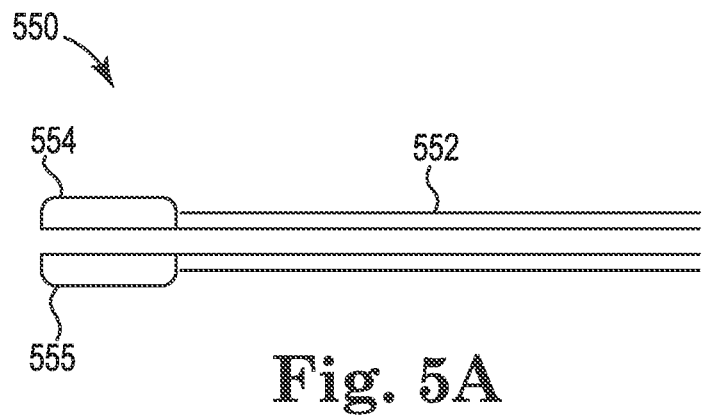
FIGS. 5A-5B illustrate a disc blade for minimally invasive spinal fusion surgery in accordance with embodiments of the present disclosure.
Figure 5B:
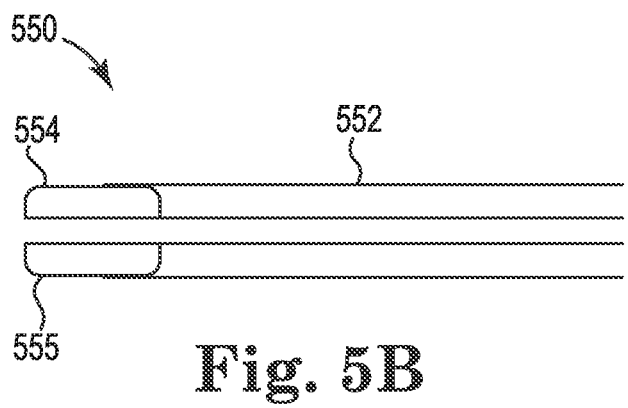

FIGS. 5A-5B illustrate a disc blade for minimally invasive spinal fusion surgery in accordance with embodiments of the present disclosure. FIGS. 5A and 5B show the distal end of disc blade 550. The distal end of disc blade 550 can move between an expanded position shown in FIG. 5A and a retracted position shown in FIG. 5B. The distal end is attached to shaft 552 which has an opening to allow the retraction of the disc blades 554 and 555. Disc blades 554 and 555 can be in the retracted position as the disc blade is moved to the spinal column via a working channel device, as shown in FIG. 5B. Disc blade 554 and 555 can be extended to an expanded position, as shown in FIG. 5A, to cut the disc up into pieces that can be removed through the working channel device. Disc blade 550 can include a proximal end including a handle that is protruding outside of the proximal end of working channel device allowing the surgeon to hold and manipulate the disc blade 550 via the handle of the disc blade 550.

Figure 6:
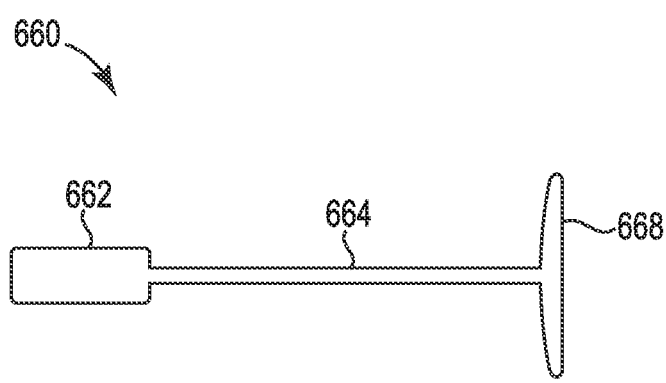
FIG. 6 illustrates a disc shaver for minimally invasive spinal fusion surgery in accordance with embodiments of the present disclosure.

FIG. 6 illustrates a disc shaver for minimally invasive spinal fusion surgery in accordance with embodiments of the present disclosure. FIG. 6 shows disc shaver 660 used to prepare the vertebral body surfaces adjacent to the removed disc for a permanent implant. Disc shaver 660 includes flat distal tip 662, shaft 664, and handle 668. The distal tip 662 of disc shaver 600 can advanced to the space from where the disc was removed and manipulated to remove any residual pieces of the disc and to clean the end plates of the vertebral body and a number of surfaces of vertebra adjacent to the vertebral disc with a flat surface of a distal tip of the disc shaver. In some embodiments, distal tip 662 can be about 6 to 10 mm wide, and can preferably be about 8 mm wide. The handle 668 on the proximal end of disc shaver 660 is can be configured to protruding outside of the proximal end of a working channel device allowing the surgeon to hold and manipulate the disc shaver 660 via the handle 668.

Figure 7A:
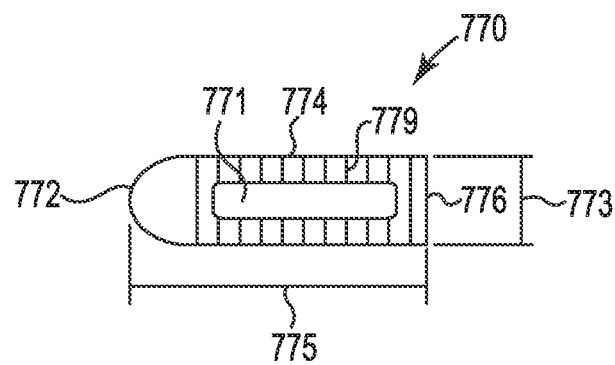
FIGS. 7A-7D illustrate a disc implant and a delivery device for minimally invasive spinal fusion surgery in accordance with embodiments of the present disclosure.
Figure 7B:
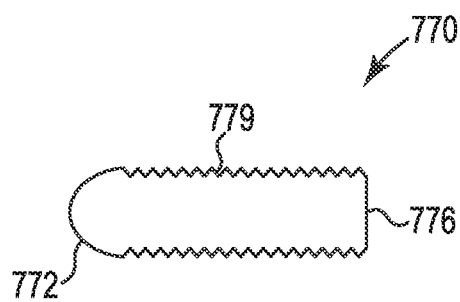
Figure 7C:
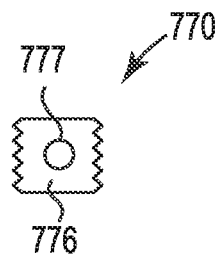
Figure 7D:
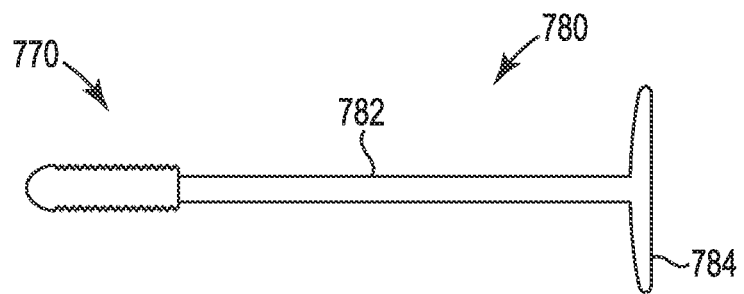

FIGS. 7A-7D illustrate a disc implant and a delivery device for minimally invasive spinal fusion surgery in accordance with embodiments of the present disclosure. FIGS. 7A-7C show disc implant 770. FIG. 7D shows disc implant 770 coupled to delivery device 780. Disc implant 770 comprises a tip region 772. Preferably tip 772 is tapered or has decreased height and width as compared to the implant main body 774. As shown in FIG. 7C, proximal end 776 includes aperture 777 that is threaded and can be used to attach the disc implant 770 to delivery device 780. Disc implant 770 can include a main body 774 that forms a cage with openings (e.g., graft window 771), on both the top and the bottom of disc implant 770. Prior to implanting, window 771 can be filled with an autograft, allograft or synthetic bone material to aid in the growth of the implant into the adjacent vertebral bones. FIG. 7A is a top view of the disc implant 770 and FIG. 7B is a side view of the disc implant 770. As shown in the top view of FIG. 7A and the side view of FIG. 7B, the main body of disc implant 770 has serrated or bumpy edges 779 to aid in ensuring that disc implant 770 stays in the proper position prior to the bone regrowth.

FIG. 7D shows the delivery device 780 coupled to disc implant 770. Delivery device 780 has a distal end of shaft 782 that attaches to disc implant 770. The distal end of shaft 782 can have a threaded connection that mates with aperture 777 of disc implant 770 to secure the disc implant 770 to the delivery device 780, while other attachment mechanisms can be used. Delivery device 780 includes shaft 782 and handle 784. Delivery device 780 can include a proximal end including handle 784 that can protrude outside of the proximal end of a working channel device allowing the surgeon to hold and manipulate the delivery device 780 and the attached disc implant via the handle 784. Handle 784 can also be used manipulate the delivery device 780 so that the threaded distal end of the delivery device 780 can be detached from the threaded aperture 777 of disc implant 770.

In a number of embodiments, the top, bottom, and/or other surfaces of disc implant 770 can be coated with hydroxyapatite (HA) or collagen type I or other osseoconductive and/or porous coatings to enhance bone ingrowth. Main body 774 of disc implant 770 may be made from a porous biocompatible material or from Ti, CoCr or other suitable alloys.

Once the vertebral space has been prepared, the surgeon will insert the implant using delivery tool into the space that once contained the vertebral disc. Once in place and when the surgeon has it positioned properly, handle 784 can be rotated to separate (e.g., detach) the disc implant 770 from the delivery device 780.

Disc implant 770 can have a length 775 of about 26 to 34 mm, preferably 28 to 32 mm. In some embodiments, lengths 775 of 28, 29, 30, 31, and 32 mm will be available. Disc implant can have a width 773 of about 8 to 10 mm, preferably 9 mm. Disc implant 770 can have a height 778 ranging from about 8 to 16 mm and can be available in heights of 8, 9, 10, 11, 12, 13, 14, 15, and 16 mm. In some embodiments, due to the normal curve of the spine, the body of disc implant 770 may be tapered.

The tools described above can be used in an oblique lumbar interbody fusion (OLIF) procedure. In an OLIF procedure, a patient is positioned on their side and an incision is made. Aided by fluoroscopy, an electrode is inserted through the incision, traverses the retroperitoneal space, and pierces the iliopsoas fascia. Once contact with the disc is made, the electrode is stimulated at to verify there is no contact with the nerve root. Once in place, a sleeve is pushed down over the electrode. The electrode is removed and a K-wire (e.g., guide 102 in FIG. 1) is inserted past the midline into the disc. The sleeve is removed, and a dilator (e.g., dilator 104 in FIG. 1) introduced over the K-wire, gently dilating the tissue. Once the dilator is entered into the disc space, the working channel device (e.g., working channel device 106 in FIG. 1) is delivered over it and pushed into the disc and the dilator and K-wire are removed. Disc material can be cut into pieces with the disc extractor and disc blade and removed with the disc rake. The disc shaver can be used to prepare and clean the endplates of the adjacent vertebral sections. The K-wire can be replaced, and the working channel device can be removed. At this stage, cage width and height of the disc implant can be determined using a trial spacer. Next, a disc implant is inserted aided by fluoroscopy. The disc implant can have a tapered conical distal end shape to aid in passing through the muscle fascia and gently pushes the nerve root out of the way. The disc implant can be advanced until approximately ⅓ of the cage is past the midline. To complete the surgery, the patient undergoes percutaneous posterior pedicle screw fixation wherein pedicle screws provide anchor points on the spinal segments (e.g., vertebra adjacent to the disc that was removed) and a metal rod is used to connect the segments together.

The present invention may be embodied in other specific forms without departing from its spirit or essential characteristics. For example, other tools may be used in the surgery or the steps may be performed in an order that is different from what was disclosed.

The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for performing a minimally invasive oblique lateral interbody fusion surgery, the method comprising:
    accessing a spinal column through a working channel device, wherein the working channel device has a proximal end and a distal end;
    advancing the working channel device so that the distal end pierces an outer layer of a vertebral disc;
    inserting a disc extractor through the working channel device and into the vertebral disc to cut the vertebral disc into pieces;
    inserting a disc blade through the working channel device and into the vertebral disc to cut the vertebral disc into pieces;
    using a disc rake to remove the pieces of the vertebral disc;
    inserting a disc shaver to clean a number of surfaces of vertebra adjacent to the vertebral disc; and
    inserting and implanting a disc implant in a space from where the vertebral disc was removed.

2. The method of claim 1, further including cutting the vertebral disc into pieces with a serrated edge of a distal end of the disc extractor.

3. The method of claim 1, further including extending a distal end of the disc blade from a retracted position within a shaft of the disc blade to an expanded position and cutting the vertebral disc with the distal end of the disc blade.

4. The method of claim 1, further including using the disc rake to remove the pieces of the vertebral disc by opening and closing a distal tip of the disc rake, via actuation of a handle of the disc rake, to grasp the pieces of the vertebral disc.

5. The method of claim 1, further including cleaning the number of surfaces of vertebra adjacent to the vertebral disc with a flat surface of a distal tip of the disc shaver.

6. The method of claim 1, further including inserting and implanting the disc implant by attaching a delivery device to the disc implant, advancing the disc implant and the delivery device to the space where the vertebral disc was removed, disconnecting the delivery device from the disc implant; and removing the delivery device.

7. The method of claim 1, further including attaching the disc implant to the vertebra adjacent to the disc implant with a number of screws and a number of rods.

8. A method for performing a minimally invasive oblique lateral interbody fusion surgery, the method comprising:
    accessing a spinal column through a working channel device, wherein the working channel device has a proximal and distal end and wherein the working channel device is advanced to the spinal column over a guide and a dilator;
    removing a vertebral disc with a number of tools, wherein a portion of the number of tools access the vertebral disc via the working channel; and inserting and implanting a disc implant in a space from where the vertebral disc was removed,
    wherein removing the vertebral disc includes cutting the vertebral disc into pieces with a disc extractor and a disc blade, and opening and closing a distal tip of a disc rake, via actuation of a handle of the disc rake, to grasp the pieces of the vertebral disc.

9. The method of claim 8, wherein inserting and implanting comprises:
attaching a delivery device to the disc implant, advancing the disc implant and the delivery device to the space from where the vertebral disc was removed, disconnecting the delivery device from the disc implant; and removing the delivery device.

10. The method of claim 8, further including placing bone graft material into an interior of a cage of the disc implant via a number of openings of the cage.

11. The method of claim 8, further including attaching the disc implant to vertebra adjacent to the disc implant via a number of screws and a number of rods.

12. A minimally invasive oblique lateral interbody fusion surgery system, the system comprising:
a working channel device configured to provide access to a spinal column, wherein the working channel device has a proximal end and a distal end;
a disc extractor configured to cut a vertebral disc of the spinal column into a first number of pieces, wherein the disc extractor is configured to access the vertebral disc of the spinal column via the working channel device;
a disc blade configured to cut the vertebral disc of the spinal column into a second number of pieces, wherein the disc blade is configured to access the vertebral disc of the spinal column via the working channel device;
a disc rake configured to remove the first and second number of pieces of the vertebral disc;
a disc shaver configured to clean a number of surfaces of vertebra adjacent to the vertebral disc; and
a delivery device configured to insert and implant a disc implant in a space from where the vertebral disc was removed.

13. The system of claim 12, wherein a serrated edge of a distal end of the disc extractor disc extractor is configured to cut the vertebral disc into the first number of pieces.

14. The system of claim 12, wherein the disc blade is configured to access the vertebral disc, via the working channel device, with a number of blades in a retracted position and to cut the vertebral disc into the second number of pieces with the number of blades in an expanded position.

15. The system of claim 12, wherein the disc rake is configured to open and close a distal tip of the disc rake, via actuation of a handle of the disc rake, to grasp and remove the first and second number of pieces of the vertebral disc.

16. The system of claim 12, wherein a flat surface of a distal tip of the disc shaver is configured to clean the number of surfaces of vertebra adjacent to the vertebral disc.

17. The system of claim 12, wherein the disc implant comprises a tapered distal end and a proximal end with a threaded connection configured to mate with a threaded connection on a distal end of the delivery device.

18. The system of claim 12, wherein the disc implant is made from an osseoconductive material and wherein this disc implant includes a number of openings configured to receive a bone graft material that is an autograft, allograft or synthetic bone material.

\* \* \* \* \*